US010697982B2

(12) United States Patent
Stone et al.

(10) Patent No.: US 10,697,982 B2
(45) Date of Patent: *Jun. 30, 2020

(54) METHODS OF EVALUATING QUALITY OF A CHROMATOGRAPHY MEDIA WHICH BINDS ANTI-A OR ANTI-B ANTIBODIES

(71) Applicant: Merck Patent GmbH, Darmstadt (DE)

(72) Inventors: Matthew T. Stone, Arlington, MA (US); Nanying Bian, Lexington, MA (US); Santosh Rahane, Acton, MA (US)

(73) Assignee: Merck Patent GmbH, Darmstadt (DE)

( * ) Notice: Subject to any disclaimer, the term of this patent is extended or adjusted under 35 U.S.C. 154(b) by 647 days.

This patent is subject to a terminal disclaimer.

(21) Appl. No.: 15/226,419

(22) Filed: Aug. 2, 2016

(65) Prior Publication Data

US 2017/0067914 A1    Mar. 9, 2017

Related U.S. Application Data

(60) Provisional application No. 62/215,423, filed on Sep. 8, 2015.

(51) Int. Cl.
*G01N 33/80* (2006.01)
*B01D 15/38* (2006.01)
*C07K 1/22* (2006.01)
*B01D 15/20* (2006.01)

(52) U.S. Cl.
CPC ............ *G01N 33/80* (2013.01); *B01D 15/20* (2013.01); *B01D 15/3809* (2013.01); *C07K 1/22* (2013.01)

(58) Field of Classification Search
None
See application file for complete search history.

(56) References Cited

U.S. PATENT DOCUMENTS

| | | | |
|---|---|---|---|
| 4,137,401 A | 1/1979 | Lemieux et al. | |
| 4,195,174 A | 3/1980 | Lemieux et al. | |
| 4,362,720 A | 12/1982 | Lemieux et al. | |
| 4,404,188 A | 9/1983 | Donahoe et al. | |
| 4,664,913 A | 5/1987 | Mielke et al. | |
| 5,149,425 A | 9/1992 | Mazid | |
| 5,541,294 A | 7/1996 | Horowitz et al. | |
| 8,153,382 B2 | 4/2012 | Chtourou et al. | |
| 2006/0073534 A1 | 4/2006 | Kelly et al. | |
| 2009/0074749 A1 | 3/2009 | Chtourou et al. | |
| 2010/0181254 A1 | 7/2010 | Graalfs | |
| 2012/0039886 A1 | 2/2012 | Elzaabi | |
| 2013/0046056 A1 | 2/2013 | Spector et al. | |
| 2015/0111194 A1 | 4/2015 | Rempfer et al. | |

FOREIGN PATENT DOCUMENTS

| | | |
|---|---|---|
| CA | 2385179 A1 | 4/2001 |
| CN | 1276527 A | 12/2000 |
| CN | 101678318 A | 3/2010 |
| CN | 103394084 A | 11/2013 |
| CN | 104053462 A | 9/2014 |
| EP | 0488755 A1 | 6/1992 |
| EP | 1224462 A2 | 7/2002 |
| EP | 1451589 A2 | 9/2004 |
| EP | 2202310 A2 | 6/2010 |
| EP | 2358391 B1 | 12/2014 |
| FR | 3008097 A1 | 1/2015 |
| FR | 3008098 A1 | 1/2015 |
| JP | 4-203967 A | 7/1992 |
| JP | 07/242698 A | 9/1995 |
| JP | 2003-511468 A | 3/2003 |
| JP | 2009-521520 A | 6/2009 |
| JP | 2010-528271 A | 8/2010 |
| JP | 2012-229212 A | 11/2012 |
| JP | 2012-254981 A | 12/2012 |
| JP | 2013-151507 A | 8/2013 |
| JP | 2014-531966 A | 12/2014 |
| KR | 10-1207797 B1 | 11/2012 |
| WO | 2001/27623 A2 | 4/2001 |
| WO | 2003/043403 A2 | 5/2003 |
| WO | 2009/154375 A2 | 12/2009 |
| WO | 2010/076496 A1 | 7/2010 |
| WO | 2013/062479 A1 | 5/2013 |
| WO | 2015/001277 A1 | 1/2015 |
| WO | 2015/034566 A1 | 3/2015 |
| WO | 2015/049651 A1 | 4/2015 |

OTHER PUBLICATIONS

Extended European Search Report received for European Patent Application No. 16187836.8, dated Feb. 1, 2017, 10 pages.
Extended European Search Report received for European Patent Application No. 16187837.6, dated Feb. 1, 2017, 9 pages.
Extended European Search Report received for European Patent Application No. 16187838.4, dated Jan. 31, 2017, 8 pages.
Rogers et al.,"Development of a Rapid Sanitization Solution for Silica-Based Protein A Affinity Adsorbents", Journal of Chromatography A, vol. 1216, Issue 21, Mar. 28, 2009, pp. 4589-4596.
Schulte et al.,"Comparative Affinity Chromatographic Studies Using Novel Grafted Polyamide and Poly(vinyl alcohol) media", Journal of Chromatography, vol. 539, Issue 2, 1991, pp. 307-314.
Tu et al.,"Preparation and Characterization of Novel IgG Affinity Resin Coupling Anti-Fc Camelid Single-Domain Antibodies", Journal of Chromatography B: Biomedical Sciences & Applications, vol. 983-984, Jan. 14, 2015, pp. 26-31.
Solovan et al., "Synthetic Blood Group Antigens for Anti-A Removal Device and Their Interaction With Monoclonal Anti-A IgM", Transplant Immunology, vol. 16, Dec. 31, 2006, pp. 245-249.

(Continued)

*Primary Examiner* — Joseph Woitach

(74) *Attorney, Agent, or Firm* — EMD Millipore Corporation

(57) ABSTRACT

Embodiments described herein relate to methods of evaluating quality of a chromatography media for removal of anti-A or anti-B antibodies from a sample, where the methods employ use of purified monoclonal IgM-A and IgM-B antibodies.

21 Claims, 1 Drawing Sheet

(56) References Cited

OTHER PUBLICATIONS

"Strategies to Address Hemolytic Complications of Immune Globulin Infusions", FDA, Centre for Biologics Evaluation and Research, Center for Drug Evaluation and Research, Workshop on Risk Mitigation Measure Strategies, Jan. 28, 2014, 348 pages.

Alikhani et al., "High Molecular Weight Blood Group A Trisaccharide-Polyacrylamide Glycoconjugates as Synthetic Blood Group A Antigens for Anti-A Antibody Removal Devices", Journal of Biomedical Materials Research Part B: Applied Biomaterials, vol. 91, 2009, pp. 845-854.

Christensson et al., "Flow Cytometric Quantitation of Serum Anti-D in Pregnancy", Transfusion,vol. 36, Issue 6, Jun. 1996 , pp. 500-505.

Crawford et al., "Practical Application of Synthetic A and B Blood Group Immunoadsorbents", Blood Transfusion and Immunohaematology, vol. 24, Issue 3, 1981, pp. 281-287.

Gautam et al., "Monoclonal Anti-A Antibody Removal by Synthetic A Antigen Immobilized on Specific Antibody Filters", Biotechnology and Bioengineering, vol. 99, No. 4, Mar. 1, 2008, pp. 876-883.

Lemieux, R.U., "Human Blood Groups and Carbohydrate Chemistry", Haworth Memorial Lecture, Chemical Society Reviews, vol. 7, 1978, pp. 423-452.

Lockyer et al., "Absorption of Unwanted Anti-A-B Agglutinins from Anti-Rh D Grouping Sera Using Time-Expired Formalised Heat-Treated A1 B Rh D Positive Red Cells", Vox Sanguinis, vol. 12, Issue 1, Jan. 1967, pp. 75-77.

McDonald et al., "A New Monoclonal Anti-A Antibody BIRMA-1: A Potent Culture Supernatant Which Agglutinates Ax Cells, but Does Not Give Undesirable Reactions with B Cells", Vox Sanguinis, vol. 61, Issue 1, Aug. 1991, pp. 53-58.

Oyen et al., "Use of *Escherichia coli* 086: B7 in the Adsorption of Anti-A and Anti-B from Blood Typing Sera", Transfusion, vol. 12, Issue 2, Mar. 4, 1972, pp. 98-102.

Bensinger et al., "Immunoadsorption for Removal of A and B Blood-Group Antibodies", New England Journal of Medicine, vol. 304, Issue 3, Jan. 15, 1981, pp. 160-162.

Bensinger et al., "In Vitro and in Vivo Removal of Anti-A Erythrocyte Antibody by Adsorption to a Synthetic Immunoadsorbent", Transfusion, vol. 21, Issue 3, May-Jun. 1981, pp. 335-342.

Bensinger et al., "Whole Blood Immunoadsorption of Anti-A or Anti-B Antibodies", Vox Sanguinis, vol. 48, Issue 6, Jun. 1985, pp. 357-361.

Blomberg et al.,"Improved Removal of Anti-A and Anti-B Antibodies from Plasma Using Blood-Group-Active Haptens", Vox Sanguinis, vol. 65, Issue 2, Jul. 1993, pp. 126-135.

Dhainaut et al.,"In Vitro and In Vivo Properties Differ Among Liquid Intravenous Immunoglobulin Preparations", Vox Sanguinis, vol. 104, Issue 2, Feb. 2013, pp. 115-126.

Matsui et al.,"Comparative Study of Blood Group-Recognizing Lectins Toward ABO Blood Group Antigens on Neoglycoproteins, Glycoproteins and Complex-Type Oligosaccharides", Biochimica et Biophysica Acta (BBA), vol. 1525, Issues 1-2, 2001, pp. 50-57.

Rieben et al.,"In Vitro Evaluation of the Efficacy and Biocompatibility of New, Synthetic ABO Immunoabsorbents", Transplantation, vol. 60, Issue 5, Sep. 15, 1995, pp. 425-430.

Rydberg et al.,"Characterisation of the Anti-A Antibody Response Following an ABO Incompatible (A2 to O) Kidney Transplantation", Molecular Immunology, vol. 29, Issue 4, Apr. 1992, pp. 547-560.

Rydberg et al.,"In Vitro Assessment of a New ABO Immunosorbent with Synthetic Carbohydrates Attached to Sepharose", Transplant International, vol. 17, Issue 11, Jan. 2005, pp. 666-672.

Sharon et al., "Lectins", Second Edition, Springer Publications, 2007, 04 pages.

Thorpe et al.,"International Collaborative Study to Evaluate Candidate Reference Reagents to Standardize Haemagglutination Testing for Anti-A and Anti-B in Normal Intravenous Immunoglobulin Products", Vox Sanguinis, vol. 97, 2009, pp. 160-168.

METHODS OF EVALUATING QUALITY OF A CHROMATOGRAPHY MEDIA WHICH BINDS ANTI-A OR ANTI-B ANTIBODIES

CROSS-REFERENCED TO RELATED APPLICATIONS

The present application claims the benefit of priority of U.S. Provisional Patent Application No. 62/215,423, filing date Sep. 8, 2015, the entire content of which is incorporated herein in its entirety.

BACKGROUND

Human plasma enriched in immunoglobulins is used for the treatment of many disorders as well as to treat certain congenital deficiencies. Typically, human plasma is obtained by pooling the plasma from multiple donors, having different blood group types. Blood group types may be divided into 4 major types. Blood group type A—having only the A antigen on red cells (and B antibody in the plasma); blood group type B—having only the B antigen on red cells (and A antibody in the plasma); blood group type AB—having both A and B antigens on red cells (but neither A nor B antibody in the plasma); and blood group type O—having neither A nor B antigens on red cells (but both A and B antibody are in the plasma).

It is important that the red bloods cells of a person having a particular blood group type antigen, such as A, never come in contact with the antibodies that will bind to this antigen, such as anti-A antigen antibodies, because contact with such antibodies would result in agglutination and/or hemolysis of their red blood cells that can even result in death. Therefore, a recipient having blood group type A may only receive plasma from a donor having blood group type A or blood group type AB; a recipient having blood group type B may only receive plasma from a donor having blood group type B or blood group type AB; a recipient having blood group AB may only receive plasma from a donor having blood group type AB; and a recipient having blood group type O is deemed a universal recipient. Compatibility of the different blood group types is important for the development of safe blood transfusions and organ transplants. However, in case of blood derived therapeutic drugs that rely on pooling of blood plasma from a large numbers of people to obtain a consistent average of protein components, it becomes particularly challenging to ensure that a recipient does not receive non-compatible plasma.

A number of approaches have been developed to selectively remove blood group type antibodies from plasma, including formalinized heat-treated red cells (Vox Sang., 1967, 12, 75-77), heat treated *Escherichia coli* $O_{86}$:B7 having A and B antigens (Transfusion, 1972, 12, 98-102), red cell stroma powder, red cell stroma antigen derived immunoadsorbents (Chemical Soc. Rev., 1978, 7, 423-452), and synthetic blood group A and B immunoadsorbents (Rev. Fr. Transfus. Immunohematol. 1981, 24, 3, 281-287).

Solid phase chromatography immunoadsorbents have been developed as commercial chromatography media for the treatment of blood derived products and also for the preparation of donors before transplantation to an ABO incompatible recipient. One of the key advantages of employing synthetic immunoadsorbents is that they are synthetically constructed instead of being derived from natural sources and therefore have more consistent properties from batch to batch.

Currently, some of the commercially available chromatographic media with blood group A antigen (A-antigen) ligands and/or blood group B antigen (B-antigen) ligands include the Glycosorb-ABO device (Glycorex Transplantation AB). This Glycosorb device is used to prepare organ donors for transplantation to patients having incompatible blood types. The blood group antigen ligands in the Glycosorb-ABO device bind and remove the blood group A antigen antibodies (anti-A) and blood group B antigen antibodies (anti-B) from the blood of organ donors thus reducing the risk of organ rejection.

One of the major challenges in utilizing chromatography media for the purification of blood derived products is the lack of an efficient and reproducible method to evaluate the relative quality of different media, e.g., different batches of same type of media or media from different sources or the same media samples over time.

SUMMARY

Embodiments described herein relate to methods of assessing quality of a chromatography media containing blood group A antigen ligand or blood group B antigen ligand. Methods described herein are especially useful for assessing or evaluating quality of same type of media from batch to batch, during and after use and for optimizing the media during development.

In some embodiments, a method for comparing quality of two or more affinity chromatography media samples is provided, both containing blood group A antigen ligands attached to a solid support, where the method comprises the steps of: (a) providing two or more affinity chromatography media samples, each of volume VR; (b) incubating each sample with a solution of purified monoclonal IgM-A antibody of known concentration C1 and volume VM; (c) obtaining a supernatant for each of the samples and measuring the concentration C2 of the IgM-A antibody in each supernatant; determining the static binding capacity of each of the affinity chromatography media samples using the following equation.

$$\frac{[C1 - C2] \times VM}{VR}$$

wherein the static binding capacities of the media samples for IgM-A correlates with their ability to remove anti-A antibodies from a sample, thereby providing a comparison of the quality of the two or more different affinity chromatography media samples.

In other embodiments, a method for comparing quality of two or more affinity chromatography media samples is provided, each containing blood group B antigen ligands attached to a solid support, where the method comprises the steps of: (a) providing two or more affinity chromatography media samples, each of volume VR; (b) incubating each sample with a solution of purified monoclonal IgM-B antibody of known concentration C1 and volume VM; (c) obtaining a supernatant for each of the samples and measuring the concentration C2 of the IgM-B antibody in each supernatant; determining the static binding capacity of each of the affinity chromatography media samples using the following equation.

$$\frac{[C1 - C2] \times VM}{VR}$$

wherein the static binding capacities of the media samples for IgM-B correlates with their ability to remove anti-B antibodies from a sample, thereby providing a comparison of the quality of two or more affinity chromatography media samples.

A media sample having higher binding capacity for IgM-A or IgM-B, relative to other samples it is compared with, is of better quality compared to the other media samples.

In some embodiments according to the methods described herein, the solid support is a porous or non-porous polymeric solid support comprising a polymer selected from the group consisting of polyvinylether, polyvinylalcohol, polymethacrylate, polyacrylate, polystyrene, polyacrylamide, polymethacrylamide and polycarbonate. In a particular embodiment, the solid support is a polyvinylether based solid support. In some embodiments, the solid support is in bead form (e.g., a polyvinyl ether based bead).

In some embodiments described herein, the different affinity chromatography media samples constitutes different batches of the same type of media.

In other embodiments, the different affinity chromatography media samples constitute the same media at different stages of use.

In some embodiments, the media are capable of removing anti-A or anti-B antibodies from a sample selected from the group consisting of blood, blood products, plasma, plasma derivatives and IVIG.

In some embodiments, the concentration of IgM-A or IgM-B antibody in supernatant is measured using absorbance at 280 nm.

Also provided herein are methods of assessing quality of an affinity chromatography media containing blood group A antigen ligand or blood group B antigen ligand attached to a solid support, following exposure of the affinity chromatography media to acid or alkaline conditions, the method comprising the steps of: (a) providing a chromatography media having either blood group A antigen ligands or blood group B antigen ligands attached to a solid support; (b) measuring the binding capacity of the media for a purified IgM-A antibody in case of blood group A antigen ligand media or for a purified IgM-B antibody in case of blood group B antigen ligand media; (c) exposing the media to acid or alkaline conditions for at least 5 hours; and (d) measuring the binding capacity of the media for a purified IgM-A antibody in case of blood group A antigen ligand media or for a purified IgM-B antibody in case of blood group B antigen ligand media; wherein a reduction in the binding capacity of media in step (d) relative to step (b) indicates that the quality of media has reduced following exposure to acid of alkaline conditions.

The embodiments described herein can also be used for determining whether a media comprises blood group A antigen ligands or blood group B antigen ligands, where the method comprises the steps of: (a) providing a media, where it is unknown whether the media comprises blood group A antigen ligands or blood group B antigen ligands; (b) measuring the binding capacity of the unknown media for purified monoclonal IgM-A antibody and separately for purified monoclonal IgM-B antibody; and (c) comparing the capacity of the unknown media for purified monoclonal IgM-A antibody and purified monoclonal IgM-B antibody; where the unknown media is determined to comprise blood group A antigen ligands, if it has a higher binding capacity for monoclonal IgM-A antibody relative to binding capacity for monoclonal IgM-B antibody, and the unknown media is determined to comprise blood group B antigen ligands if it has a higher binding capacity for monoclonal IgM-B antibody relative to binding capacity for monoclonal IgM-A antibody.

In some embodiments, an unknown media is determined to comprise blood group A antigen ligands if it has binding capacity for a monoclonal IgM-A antibody and no binding capacity for a monoclonal IgM-B antibody. Conversely, an unknown media is determined to comprise blood group B antigen ligands if it has binding capacity for a monoclonal IgM-B antibody and no binding capacity for a monoclonal IgM-A antibody.

DETAILED DESCRIPTION

Figure 1:
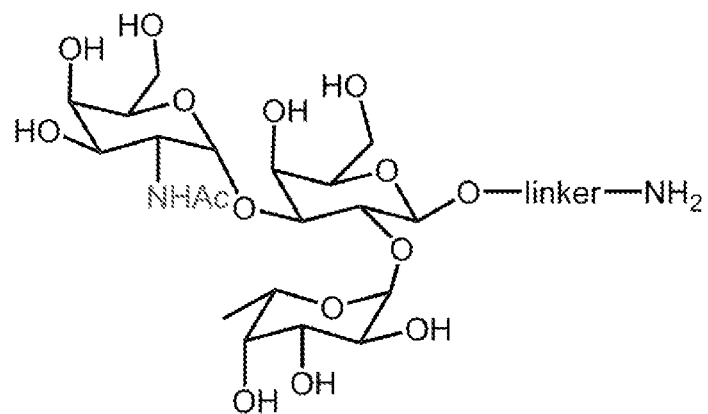
FIG. 1 is a representative oligosaccharide ligand, which binds anti-A antigen antibodies.

Recently there has been an increased interest in the application of synthetic immunoadsorbent chromatography media for the removal of anti-A and anti-B IgG from intravenous immunoglobulin (IVIG), which consists of concentrated polyvalent IgG antibodies extracted from pooled plasma obtained from several blood donors, sometimes as many as thousand or greater than thousand blood donors. During the process of purifying the IgG from blood plasma, the larger anti-A and anti-B IgM antibodies can typically be separated from the smaller IgG antibodies by fractionation. However, some percentage of the anti-A and anti-B antibodies are generally in the form of IgG that cannot be distinguished from the other IgG antibodies by fractionation alone. Thus, IVIG therapeutic concentrates are typically screened using an agglutination assay to monitor the concentrations of anti-A and anti-B IgG antibodies in order to prevent administration of IVIG with high concentrations of anti-A and anti-B IgG antibodies. However, despite this precaution, hemolytic reactions that can lead to death, are still known to occur for those recipients having blood group types A, B, or AB (Transcript for "Strategies to address hemolytic complications of immune globulin infusions," FDA Center for Biologics Evaluation and Research Public Workshop Washington, D.C. Jan. 28-29, 2014).

Common agglutination assays rely on the use of live red blood cells, which have limited lifetimes and the density of antigens on the cell surface generally vary from lot to lot. Agglutination also requires serial dilutions and relies on a qualitative evaluation (visual or microscopic observations) of cell agglutination. A more accurate method to determine the concentrations of anti-A and anti-B antibodies employs flow-cytometry. However, flow-cytometry methods also use live red blood cells and are significantly more complex and time consuming than agglutination assays. ELISA assays have also been reported to measure the concentration of anti-A and anti-B antibodies, however this technique requires a relatively complex multistep procedure and specialized antigen reagents.

As discussed above, chromatography immunoadsorbent media containing ligands that bind anti-A or anti-B antibodies are considered effective for the removal of such antibodies from blood derived products, e.g., plasma and IVIG. However, currently, there are no good methods available which may be used for qualification and validation of such media, in order to assess their reproducibility and reliability.

It is important to evaluate the batch-to-batch quality of blood group antigen ligand chromatography media in order to ensure that the media meets production specifications and quality requirements throughout its lifetime. Further, it is also important to evaluate such media during and after use, cleaning and sanitization to make sure that it retains the ability to remove the intended impurities following use, cleaning and sanitization procedures. The ability of blood group antigen ligand media to bind their intended target molecules has usually been evaluated directly by measuring the reduction in the concentration of polyclonal blood group antigen antibodies in blood derived products before and after contact with the blood group antigen ligand media.

As evidenced by the Examples herein, the capacity of anti-A and anti-B antigen ligand media for a purified IgM monoclonal antibody correlates with the ability of the media to remove blood group A antibodies or blood group B antibodies, as the case maybe, from an IVIG feed. This finding was rather unexpected due to the inherent differences between the type and size of IgG and the IgM molecules. In other words, IgM has a pentameric structure and the binding capacity of a media for an IgM molecule, which has a pentameric structure, would not be expected to correlate with that media's ability to remove IgG molecules having a monomeric structure. Furthermore, as evidenced by the Examples described herein, the binding capacity of a media for a murine IgM antibody is predictive of its ability to remove a percentage of human IgG molecules from a sample, e.g., an IVIG feed, i.e., from a completely different species, which was also unexpected.

Measuring the capacity of the blood group antigen ligand containing media for a purified molecule (e.g., IgM in this case) has several advantages over previously described methods, which largely relied on measuring the removal of blood group antigen antibodies from blood products, which is both time consuming and difficult to reproduce. In contrast, the embodiments described herein rely on measuring the binding capacity for a purified molecule that can be performed more efficiently and reproducibly compared to the conventional methods known in the art.

Specifically, not only are the methods described herein more easily reproducible since consistent concentrations of the monoclonal antibodies can be prepared for each capacity measurement but the methods described herein also do not require any specialized equipment (e.g., for flow-cytometry) or any specialized blood group antigen reagents (e.g., for ELISA based assays).

In order that the embodiments disclosed herein may be more readily understood, certain terms are first defined. Additional definitions are set forth throughout the detailed description.

I. Definitions

The term "binding capacity" refers to the amount of a molecule which binds to a defined volume of media packed in a column and run under defined conditions The binding capacity of a chromatography media described herein is the amount of anti-A or anti-B antibodies that the chromatography media can bind per volume of media at a set flow rate.

In the embodiments described herein, purified IgM monoclonal antibody is used to evaluate the binding capacity of a chromatography media suitable for removing anti-A or anti-B antibodies; and such binding capacity correlates with the ability of such media to remove anti-A or anti-B antibodies. In other words, the binding capacity of a chromatography media for IgM can be used as an indicia to determine the effectiveness of the media to remove anti-A or anti-B antibodies, as the case may be. The binding capacity may be measured as static binding capacity or dynamic binding capacity.

The term "static binding capacity" of a media (e.g., a chromatography media) is defined as the amount of a protein bound by the media divided by the volume of the media used. An exemplary method for measuring the static binding capacity of a chromatography media is as follows. After contacting the chromatography media with the protein solution of known concentration, the solution is allowed to incubate with the media to facilitate binding of the protein to the chromatography media. The incubation time may vary (e.g., from 5 minutes to 72 hours) and can be readily determined by one of ordinary skill in the art, e.g., by measuring the concentration of the protein in the supernatant periodically (e.g., by measuring absorbance at 280 nm) until there is no measurable change in the concentration in the supernatant. Once equilibrium is reached between the protein bound to the chromatography media and that in solution, the concentration of the protein solution is once again measured in the supernatant. The static binding capacity is then measured by the starting amount of protein (before incubation) minus the amount of protein in the supernatant (after incubation) divided by the volume of the media used.

The static binding capacity of a particular chromatography media is generally influenced by the composition of the protein solution including one or more of the following factors, e.g., concentration of the protein, amount of chromatographic media used, concentration of other components in the solution (salts, organic molecules, buffers), the solution pH, and conductivity. It may also be influenced by the temperature of the protein solution. All of these variables are generally held constant in order to allow the comparison of static binding capacity between two different chromatography media. The term "static binding capacity" may also be referred to as "saturation binding capacity" or "maximum binding capacity."

In some embodiments described herein, static binding capacity of a blood group A antigen ligand containing media or blood group B antigen ligand containing media for a purified monoclonal IgM antibody is used as an indicia to predict or assess its ability to remove anti-A or anti-B antibodies, as the case may be, from a sample (e.g., an IVIG feed). Comparing the static binding capacity of two different batches of media or the same media over time or media from different sources, is especially useful, as it provides information about the quality of the media. In other words, since the binding capacity for a purified IgM antibody correlates with its ability to remove anti-A or anti-B antibodies, as the case may be, the binding capacity can be used to evaluate and compare the performance of different batches of a media or the same media over time or media from different sources. Accordingly, using the methods described herein, one of ordinary skill or an end user in the art can readily determine whether a batch of media exhibits loss in its performance (i.e., ability to remove anti-A or anti-B antibodies) over another batch of the same type of media, or over time, especially after repeated cleaning and sanitization. Further, measurement of static binding capacity for purified IgM can also be used to optimize a media during development.

In general, the static binding capacity may be can be calculated as follows. A media sample of volume VR is incubated with a solution of purified monoclonal IgM antibody of known concentration C1 and known volume VM (IgM-A in case of blood group A antigen ligand media and IgM-B in case of blood group B antigen ligand media); a supernatant is obtained and the concentration of IgM antibody C2 is measured in the supernatant; the static binding capacity is then calculated using the following equation.

$$\frac{[C1-C2] \times VM}{VR}$$

The term "dynamic binding capacity" is defined as the amount of a protein that is bound by a chromatography column under flow conditions at the point when the concentration of the protein solution exiting the chromatography column reaches a certain concentration, typically a predetermined percentage of the starting concentration. In practice, this tends to be about 10% of the starting concentration. This mass of protein is then divided by the volume of media in the chromatography column.

The dynamic binding capacity of a particular chromatography media is generally influenced by the composition of the protein solution including one or more of the following factors, e.g., concentration of the protein, concentration of other components in the solution (salts, organic molecules, buffers), the solution pH, and conductivity. The dynamic binding capacity may also be influenced by the temperature at which the column is loaded and by the flow-rate at which the protein solution is loaded onto the column. Decreasing the flow-rate of the protein solution into the chromatography column increases the dynamic binding capacity that is measured. Conversely, increasing the flow-rate of the protein solution into the chromatography column decreases the dynamic binding capacity that is measured. The dynamic binding capacity should not exceed the static binding capacity since the dynamic capacity of a chromatography media is limited by the overall rate of mass transfer.

The term "supernatant" is defined as liquid which is above the settled chromatography media. Supernatant solution may be obtained by allowing the chromatography media in a slurry to settle to the bottom of a container or a column. The settling process can be accelerated by subjecting the slurry of chromatography media to centrifugation or by vibration. The supernatant solution can then be separated from the chromatography media by transferring via a pipetting, syringe, or pump to a separate container. Further, a supernatant may also be obtained by filtering a slurry of chromatography media through a membrane or porous material.

The term "sample" is defined as the solution containing at least one target protein (e.g., anti-A or anti-B antibody in this case) intended to be bound to a chromatography media, as described herein. In some embodiments, the target protein is an antibody or an immunoglobulin. In some embodiments, the immunoglobulin is a blood group A antigen antibody (i.e., anti-A antibody). In other embodiments, the immunoglobulin is a blood group B antigen antibody (i.e., anti-B antibody). Examples of samples include but are not limited to, blood, plasma, plasma derivatives, blood products, intravenous immunoglobulins feed (IVIG).

The term "IgG," "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form.

The term "IgM" or "Immunoglobulin M," as used herein, refers to antibodies with a pentameric structure, e.g., the IgM antibodies found in blood serum. With a molecular weight of approximately 970 kDa, IgM antibodies are considerable larger than IgG that have a monomeric structure and a molecular weight of approximately 150 kDa. Unlike IgG antibodies that have 2 antigen binding sites, IgM antibodies have 10 antigen binding sites. IgM antibodies are primarily responsible for the agglutination of red blood cells when a recipient receives a blood transfusion from an incompatible donor. For instance, a person with blood type A and having anti-B IgM antibodies will experience agglutination upon transfusion from a blood type B donor. The large IgM antibodies can generally be separated from smaller IgG antibodies in blood plasma by fractionation.

The term "chromatography" as used herein, refers to a dynamic separation technique which separates or removes a molecule (e.g., anti-A and/or anti-B antibodies in this case) from other molecules in a sample. Typically, in a chromatography method, a mobile phase (liquid or gas) transports a sample containing the molecule to be separated or removed through a stationary phase (normally solid) medium (e.g., a chromatography media). Differences in partition or affinity to the stationary phase separate the molecule from other components of the sample.

The term "affinity chromatography," as used herein, refers to a mode of chromatography where a molecule to be separated or removed (e.g., anti-A and/or anti-B antibodies) is isolated by its interaction with another molecule (e.g., a blood group A antigen ligand or blood group B antigen ligand immobilized onto a solid support) which specifically interacts with the molecule to be separated or removed. A media used in affinity chromatography is referred to as an affinity chromatography media.

The term "media" or "chromatography media," as used interchangeably herein, refers to a solid support having a blood group A antigen ligand and/or blood group B antigen ligand immobilized thereon.

The methods described herein can be used for assessing quality of any chromatography media which is suitable for removing anti-A and/or anti-B antibodies, including those described in U.S. Provisional Patent Application No. 62/215,401, filed on Sep. 8, 2015.

In the embodiments described herein, a purified IgM solution is used to evaluate the binding capacity of a chromatography media including a blood group A antigen ligand or blood group B antigen ligand attached to a solid support. In other words, purified IgM monoclonal antibody is used as a model molecule to investigate the quality of a chromatography media suitable for removing anti-A or anti-B antibodies.

The terms "anti-A" or "anti-A antibodies" refer to antibodies which bind blood group A antigens found on the surface of cells in individuals that have blood group type A or blood group type AB. Accordingly, it is desirable to remove such antibodies in blood derived samples (e.g., blood, blood products, plasma, plasma derivatives or an IVIG feed).

The terms "anti-B" or "anti-B antibodies" refer to antibodies which bind blood group B antigens found on the surface of cells in individuals that have blood group type B or blood group type AB. Accordingly, it is desirable to remove such antibodies in blood derived samples (e.g., blood, blood products, plasma, plasma derivatives or an IVIG feed).

The term "quality of a media," as used herein, refers to the ability of a chromatography media to selectively remove an undesirable entity (e.g., anti-A or anti-B antibodies) from a sample (e.g., blood, blood products, plasma, plasma derivatives or an IVIG feed). The methods provided herein are especially useful to evaluate and/or monitor the relative quality of different media (e.g., different batches of the same type of media or same type of media from different sources or media samples or prototypes obtained during development or manufacture process) by measuring their binding capacity for a purified IgM monoclonal antibody. In other words, the relative binding capacities of different media or media samples for a purified monoclonal IgM antibody is indicative of ability of the media to selectively remove anti-A or anti-B antibodies (i.e., relative quality of the media or media samples). Accordingly, the binding capacity of a media for particular IgM molecule can be used to discern the overall quality of the media relative to other batches of the same media or the quality of the same media over time, e.g., during manufacture, use, cleaning and sanitization.

Therefore, a batch of media designed to remove anti-A antibodies which has lower binding capacity for a purified IgM-A antibody than a previously manufactured batch of that same type of media would be of a poorer quality relative to the previous batch, as it would be expected to remove a lower percentage of anti-A antibodies from a sample. Conversely, a batch of media designed to remove anti-A antibodies which has higher binding capacity for a purified IgM-A antibody than a previously manufactured batch of that same type of media would be of a better quality relative to the previous batch, as it would be expected to remove a higher percentage of anti-A antibodies from a sample. Similarly, a batch of media which has lower binding capacity for a purified IgM-B antibody than a previously manufactured batch of that same type of media would be of a poorer quality relative to the previous batch, as it would be expected to remove a lower percentage of anti-B antibodies from a sample. Conversely, a media which has higher binding capacity for a purified IgM-B antibody than a previously manufactured batch of that same type of media would be of a better quality relative to the previous batch, as it would be expected to remove a higher percentage of anti-B antibodies from a sample.

There is generally a need to monitor the quality of chromatography media during its lifetime to ensure that the media retains its ability to remove a desirable percentage of anti-A antibodies or anti-B antibodies from a sample. For example, the quality of the chromatography media may be adversely affected after repeated use, e.g, following exposure to harsh cleaning and/or sanitization conditions, reducing its ability to remove a particular percentage of anti-A antibodies or anti-B antibodies from a sample. The quality of a batch of media designed to remove anti-A or anti-B antibodies can be monitored by measuring its binding capacity for a purified IgM-A antibody or IgM-B antibody, respectively, before and after the media has been repeatedly used or exposed to harsh cleaning and/or sanitization conditions. If the binding capacity of the media for a purified IgM-A or IgM-B has been reduced relative to the previous time it was measured, this would indicate that the media would now remove a lower percentage of anti-A or anti-B antibodies.

Accordingly, the methods described herein are useful for assessing quality of a chromatography media for anti-A or anti-B removal, over time, as well as comparing the quality of two separate batches of media.

Further, the methods described herein may also be used for optimization of a media during manufacture or development. In other words, a prototype media can be evaluated for its ability to remove anti-A or anti-B antibodies, as the case maybe, simply by determining its binding capacity for a purified IgM antibody, and the media can be further improved or optimized, if necessary, based on its binding capacity for a purified IgM antibody. For example, once a prototype media is made, the quality of that media can be assessed using the methods described herein, to determine whether it needs further optimization or modifications. This way, various iterations of the media can be easily evaluated for quality during development, leading to the final version of the media.

Additionally, the methods described herein are also useful for differentiating between blood group A antigen ligand media and blood group B antigen ligand media. It is easy for an operator or an end user to mistake the identity of the two media during manufacture and also when being used as the two types of media are often manufactured and also stored at the same location and appear virtually identical upon visual inspection. The methods described herein provide a way to distinguish between these two types of media, i.e., when it is unknown whether the media binds anti-A antibodies or anti-B antibodies. For example, the identity of an unknown media (i.e., whether it contains blood group A antigen ligands or blood group B antigen ligands) can be established by comparing its capacity for purified monoclonal anti-A IgM and for purified monoclonal anti-B IgM with the capacities of all possible known media for purified monoclonal anti-A IgM and for purified monoclonal anti-B IgM. Accordingly, a media containing blood group A antigen ligand would be expected to show significant binding capacity for purified IgM-A antibody and significantly lower or negligible binding capacity for purified IgM-B antibody. Similarly, a media containing blood group B antigen ligand would be expected to show significant binding capacity for purified IgM-B antibody and significantly lower or negligible binding capacity for purified IgM-A antibody.

In some embodiments, the binding capacity of an unknown media for IgM-A or IgM-B can be compared to the binding capacity of a known media of the same type for IgM-A or IgM-B (e.g., from a different batch) to determine whether it includes blood group A antigen ligands or blood group B antigen ligands.

II. Exemplary Blood Group Antigen Media

The methods described herein are useful for assessing the relative quality of different media which binds either blood group A antigen antibodies or blood group B antigen antibodies.

The methods described herein may be used for evaluating any commercially available media or media being developed, which is known to bind blood group A antigen antibodies or blood group B antigen antibodies. Further, the methods described herein may also be used for differentiating between types of media, in the event it is unknown whether the media binds blood group A antigen antibody or blood group B antigen antibody.

Examples of media which may currently be commercially available or has been commercially available at one time include, e.g., the Glycosorb ABO A-column and B column offered by Glycorex Transplantation AB (Sölvegatan 41, 223 70 Lund, Sweden); the blood group A trisaccharide Sepharose-4B—AFF201, blood group A trisaccharide Sepharose-FF—AFF101, blood group B trisaccharide Sepharose-4B—AFF202, and Blood group B trisaccharide Sepharose-FF—AFF102, offered by Dextra Laboratories Ltd (Science and Technology Centre, Earley Gate, Whiteknights Road, Reading, RG6 6BZ, United Kingdom); the Synsorb A and B media, offered by Chembiomed Ltd (Edmonton, Alberta, Canada); and the Allotran A and B media offered by Lectinity Holding, Inc. (Moscow, Russia). In general, any media may be evaluated using the methods described herein, which includes a ligand (typically an oligosaccharide based ligand) corresponding to an epitope of blood group type A antigen or blood group type B antigen attached directly or indirectly (via a linker or a spacer) to a solid support. Exemplary media can also be found in U.S. Provisional Patent Application No. 62/215,401, filed on Sep. 8, 2015. Exemplary oligosaccharide based ligands are shown below.

The abbreviations used in the structure are defined as follows: Gal=D-galactose, Fuc=L-fucose, GalNAc=N-acetyl-D-galactosamine, GlcNAc=N-acetyl-D-glucosamine, R=the linkage from the ligand to the solid support, although linkages at other positions on the ligand structure may also be used.

Examples of blood group type A antigen ligands include, but are not limited to, molecules that having the following structures: trisaccharide antigen A (GalNAc$\alpha$1,3[Fuc$\alpha$1,2]Gal$\beta$-R), tetrasaccharide antigen A Type 1 (GalNAc$\alpha$1,3[Fuc$\alpha$1,2]Gal$\beta$1,3GlcNAc$\beta$1-R), tetrasaccharide antigen A Type 2 (GalNAc$\alpha$1,3[Fuc$\alpha$1,2]Gal$\beta$1,4GlcNAc$\beta$1-R), tetrasaccharide antigen A Type 3 (GalNAc$\alpha$1,3[Fuc$\alpha$1,2]Gal$\beta$1,3GalNAc$\alpha$1-R), and tetrasaccharide antigen A Type 4 (GalNAc$\alpha$1,3[Fuc$\alpha$1,2]Gal$\beta$1,3GalNAc$\beta$1-R).

Examples of blood group type B antigen ligands include molecules that having the following structures: trisaccharide antigen B (Gal$\alpha$1,3[Fuc$\alpha$1,2]Gal$\beta$-R), tetrasaccharide antigen B Type 1 (Gal$\alpha$1,3[Fuc$\alpha$1,2]Gal$\beta$1,3GlcNAc$\beta$1-R), tetrasaccharide antigen B Type 2 (Gal$\alpha$1,3[Fuc$\alpha$1,2]Gal$\beta$1,4GlcNAc$\beta$1-R), tetrasaccharide antigen B Type 3 (Gal$\alpha$1,3[Fuc$\alpha$1,2]Gal$\beta$1,3GalNAc$\alpha$1-R), and tetrasaccharide antigen B Type 4 (Gal$\alpha$1,3[Fuc$\alpha$1,2]Gal$\beta$1,3GalNAc$\beta$1-R).

One or more of the above-mentioned ligands may be attached to a suitable solid support, thereby resulting in a chromatography media which is suitable for removing blood group A and/or blood group B antigen antibodies.

Examples of solid supports include, but are not limited to, alumina, silica, celite, ceramics, metal oxides, porous glass, controlled pore glass, carbohydrate polymers, polysaccharides, agarose, sepharose, sephadex, dextran, cellulose, starch, chitin, zeolites, synthetic polymers, polyvinyl ether, polyethylene, polypropylene, polystyrene, nylons, polyacrylates, polymethacrylates, polyacrylamides, polymaleic anhydride, membranes, hollow fibers and fibers. In some embodiments, the solid support is a polymeric solid support and comprises a polymer selected from the group consisting of polyvinylether, polyvinylalcohol, polymethacrylate, polyacrylate, polystyrene, polyacrylamide, polymethacrylamide and polycarbonate. In a particular embodiment, the solid support is a polyvinylether based solid support. In some embodiments, the solid support is in bead form (e.g., a polyvinyl ether based bead).

It is possible to employ a myriad of functional groups to facilitate attachment of a ligand to a solid support. The non-limiting examples of such functional groups include amine, thiol, furan, maleimide, epoxy, aldehyde, alkene, alkyn, azide, azlactone, carboxyl, activated esters, triazine, and sulfonyl chloride. In a particular embodiment, an amine group is used as a functional group.

The solid support may also be modified and/or activated to include one or more of the above functional groups to facilitate immobilization of a suitable ligand or ligands to the support. In a particular embodiment, a carboxyl and aldehyde groups are used as the functional groups.

III. Assay for Measuring Binding Capacity

The methods described herein are useful for assessing the relative quality of media (e.g., during or after a manufacturing process or after use) which binds or is expected to bind blood group A antigen antibodies or blood group B antigen antibodies in a sample, e.g., blood, a blood product, plasma, plasma derivatives or an IVIG feed. The methods described herein, rely, at least in part, on the measurement of the binding capacity of media for a purified monoclonal IgM-A or IgM-B antibody molecule in order to assess the relative quality of media, either over time or when comparing two different batches of a media or media from different sources. Accordingly, the methods described herein may be used to differentiate between the different batches of the same type of media or the same batch of media over its lifetime of use or even media from different sources.

In general, the binding capacity of a media for a particular molecule (e.g., an IgM antibody) can be measured as follows. A sample containing the molecule is contacted with a suitable media under appropriate conditions and for a period of time suitable to facilitate binding of the molecule to the media. Thereafter, the molecule that is bound to the media is separated from the remaining sample solution and the concentration of the molecule in the remaining sample solution (i.e., concentration of unbound molecule) is measured. The concentration of the molecule in solution can be determined by several different methods known in the art. For example, the absorbance of the solution can be measured at a particular wavelength and the concentration of the molecule can be calculated in combination with the extinction coefficient of the molecule (e.g., a protein) at that wavelength. Fluorescence, UV, or Raman absorbance can be measured to determine the protein concentration. In addition, the concentration of the molecule in solution can also be determine by analytical chromatography. The intensity of the detection is then correlated to the concentration of the molecule.

In the embodiments described herein, the binding capacity of a blood group type A ligand media or a blood group type B ligand media for a purified monoclonal IgM is measured, which is then indicative of how that media may perform for the actual removal of anti-A or anti-B antibodies, as the case may be.

Embodiments are further illustrated by the following examples which should not be construed as limiting. The contents of all references, patents and published patent applications cited throughout this application, as well as the Figures, are incorporated herein by reference.

EXAMPLES

Example 1. Synthesis of Blood Group A Antigen Trisaccharide Ligand Containing Chromatography Media This is an exemplary method which may be used for manufacturing a blood group A antigen ligand media. Blood group A antigen trisaccharide (TriA) ligand containing chromatography media was synthesized by immobilizing TriA ligands onto proprietary polyvinyl ether based beads (i.e., the solid support used herein). The specific structure of the TriA ligand is depicted in FIG. 1. The TriA ligand, in this case, also includes a linker with an amine group, which is used for immobilization onto the base beads. The beads are activated to include a reactive group such as, e.g., an epoxy, a carboxyl or an aldehyde group, which is capable of reacting with an amine group on the ligand. The TriA ligand is then immobilized onto the beads by a coupling reaction with the primary amine (—NH2) group.

Figure 2:
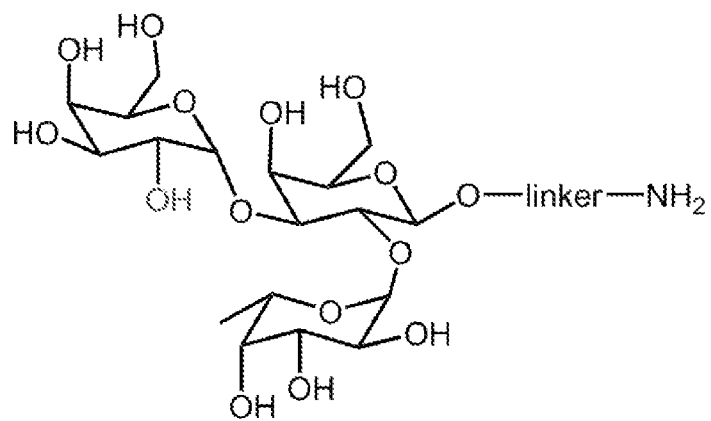
FIG. 2 is a representative oligosaccharide ligand, which binds anti-B antigen antibodies.

Example 2. Synthesis of Blood Group B Antigen Trisaccharide Ligand Containing Chromatography Media In another experiment, a blood group B antigen ligand media was made as follows. Blood group B antigen trisaccharide (TriB) ligand containing chromatography media was synthesized by immobilizing TriB ligands onto proprietary polyvinyl ether based beads (i.e., the solid support used herein). The specific structure of the TriB ligand is depicted in FIG. 2. The TriB ligand, in this case, also includes a linker with an amine group, which is used for immobilization onto the beads. As in case of the TriA ligand above, the beads are activated to include a reactive group such as, e.g., an epoxy, a carboxyl or an aldehyde group, which is capable of reacting with an amine group on the ligand. The TriB ligand is then immobilized onto the base beads by a coupling reaction with the primary amine (—NH2) group.

Example 3. Purification of Murine Monoclonal IgM-A Antibody

In the embodiments described herein, a purified monoclonal IgM antibody is used as a model molecule to assess the quality of a chromatography media which binds anti-A or anti-B antibodies. This example describes a process to purify a monoclonal IgM-A antibody; although other processes may also be used or such antibodies may be obtained commercially.

Blood group A antigen murine monoclonal IgM antibody (anti-A) was purified from commercially available clarified cell culture feed containing the anti-A IgM produced from the clone BIRMA-1 (Vox Sang., 1991, 61: 53-58) that was dialyzed into 10 mM PBS buffer (product number: JH-1L-BK, EMD Millipore, Billerica, Mass., USA). The anti-A cell culture feed was filtered through a 0.22 micron membrane and subjected to bind/elute chromatography on a media having blood group A antigen trisaccharide (TriA) ligands attached thereto, as described in Example 1.

A column 10 mm in diameter was packed to 64 mm with the Tri-A ligand media. The column was equilibrated with 10 mM PBS buffer (10 column volumes (CVs) at 305.58 cm/h, 4.0 mL/min) and subsequently loaded with the clarified cell culture feed containing anti-A in 10 mM PBS (40 CVs, 229.18 cm/h, 3.0 mL/min). The column was washed with 10 mM PBS buffer (5 CVs, 305.58 cm/h, 4.0 mL/min), followed by 0.5 M sodium chloride in 10 mM PBS buffer (10 CVs, 305.58 cm/h, 4.0 mL/min). Then, the anti-A IgM antibody was eluted from the column with 0.1 M glycine at pH 2.7 (9 CVs, 305.58 cm/h, 4.0 mL/min). The column was subsequently washed with 10 mM PBS buffer (10 CVs, 305.58 cm/h, 4.0 mL/min) and stripped with 0.5 M sodium hydroxide (10 CVs, 305.58 cm/h, 4.0 mL/min) before further runs.

1 mL of 2.0 M Tris base was added to 45 mL of the anti-A IgM eluate to increase its solution pH to 6-7. The elution was subsequently dialyzed into 10 mM PBS using dialysis tubing (Standard RC Dialysis Trial Kits, Spectra/Por® 1-3, 3.5K MWCO, 54 mm FLAT WIDTH, serial number: 132725, Spectrum Laboratories, Inc. Rancho Dominguez, Calif., 90220 USA). After dialysis in 10 mM PBS, the resulting solution of the monoclonal anti-A IgM was found to have a concentration of approximately 1.1 mg/mL based on an extinction coefficient of 1.50 at 280 nm, as determined based on the IgM antibody's amino acid composition.

Example 4. Purification of Monoclonal Murine IgM-B Antibody

Blood group B antigen murine monoclonal IgM antibody (anti-B) was purified from commercially available clarified cell culture containing the anti-B IgM produced from the clone LB-2 that was dialyzed into 10 mM PBS buffer (product number: JM-1L-BK, EMD Millipore, Billerica, Mass., USA). The anti-B cell culture feed was filtered through a 0.22 micron membrane and subjected to bind/elute chromatography on a media having blood group antigen trisaccharide (TriB) ligands attached thereto, as described in Example 2.

A column 10 mm in diameter was packed to 64 mm with the TriB ligand media. The column was equilibrated with 10 mM PBS buffer (10 CVs at 305.58 cm/h, 4.0 mL/min) and subsequently loaded with the clarified cell culture feed containing monoclonal anti-B in 10 mM PBS (40 CVs, 229.18 cm/h, 3.0 mL/min). The column was washed with 10 mM PBS buffer (5 CVs, 305.58 cm/h, 4.0 mL/min), followed by with 0.5 M sodium chloride in 10 mM PBS buffer (10 CV, 305.58 cm/h, 4.0 mL/min). Then the anti-B antibody was eluted from the column with 0.1 M glycine at pH 2.7 (9 CVs, 305.58 cm/h, 4.0 mL/min). The column was subsequently washed with 10 mM PBS buffer (10 CVs, 305.58 cm/h, 4.0 mL/min) and stripped with 0.5 M sodium hydroxide (10 CVs, 305.58 cm/h, 4.0 mL/min) before further runs.

1 mL of 2.0 M Tris base was added to 45 mL of the anti-B eluate to increase its solution pH to 6-7. The elution was dialyzed into 10 mM PBS using dialysis tubing (Standard RC Dialysis Trial Kits, Spectra/Por® 1-3, 3.5K MWCO, 54 mm FLAT WIDTH, serial number: 132725, Spectrum Laboratories, Inc. Rancho Dominguez, Calif., 90220 USA). After dialysis in 10 mM PBS, the resulting solution of the monoclonal anti-B murine IgM had a concentration of approximately 1.3 mg/mL based on an extinction coefficient of 1.44 at 280 nm, as determined based on the protein's amino acid composition.

Example 5. Binding Capacity of Blood Group A Antigen Trisaccharide Ligand Chromatography Media for Purified Murine Monoclonal IgM-A Antibody as a Measure of Media Quality This is a representative example demonstrating that the binding capacity of a blood group A antigen trisaccharide (TriA) ligand media for a purified monoclonal IgM-A antibody can be used to evaluate the variations in batch-to-batch quality of the chromatography media, e.g., during and after manufacturing.

The concentration of TriA ligands was varied during the coupling reaction with the solid support, which in this case was the polyvinyl ether based base beads. The base beads were expected to have differing amounts of the TriA ligands, which simulates the type of variation that is expected during the media manufacturing process.

The concentration of the ligand used was in the order of: TriA Media #1<TriA Media #2<TriA Media #3. It was predicted that IgM capacity would be the least for the TriA Media #1, followed by TriA Media #2, and greatest for TriA Media #3.

In this experiment, the static binding capacity of the three TriA ligand containing chromatography media for the anti-A IgM was measured. This value was compared with the percentage of anti-A IgG antibody removal from an IVIG feed Gammanorm 16.5% (165 mg/mL, 20×20 mL, product number: 00 357 340, Octapharma AG).

A set of 2.0 mL microcentrifuge tubes were filled with 0.35 mL of 10 mM PBS buffer or 0.50 mL of 10 mM PBS buffer for the controls. Subsequently, 0.15 mL of a 10% suspension of the media (15 µL media volume) in 10 mM PBS buffer was added to the microcentrifuge tubes, except for the controls, followed by the addition of 1.0 mL of a 1 mg/mL anti-A IgM monoclonal antibody solution in 10 mM PBS buffer. The tubes were allowed to rotate for 4 hours at room temperature. Subsequently, the microcentrifuge tubes were subjected to centrifugation and the resulting supernatant was transferred into centrifugal filtration devices with a 0.22 micron membrane. The devices were subjected to centrifugation and then the absorbance of the filtrate was measured at 280 nm. The solution absorbance of each sample was then used to calculate the media's static binding capacity for anti-A IgM monoclonal antibody. The anti-A IgM static binding capacity was calculated based on an extinction coefficient of 1.50 at 280 nm, which was estimated based on the protein's amino acid composition.

In another experiment, blood group A antigen polyclonal IgG antibody (anti-A) level in a representative IVIG feed was determined by an established flow cytometry method (Christensson, M. et al, Transfusion, 1996, 36, 500-505). Type A red blood cells were incubated with the representative IVIG feed for a pre-determined time, followed by extensive washes. The cells were then stained with fluorescence-labeled anti-human IgG (Alexa Fluor® 488 AffiniPure F(ab')$_2$ Fragment Goat Anti-Human IgG (H+L), part number: 109-546-088, Jackson ImmunoResearch, West Grove, Pa., USA), and subjected to Flow Cytometry (Guava 5HT, EMD Millipore). Net mean fluorescence intensity (MFI) values were used to compare anti-A polyclonal IgG concentrations in the feed before and after contact with the blood group A trisaccharide antigen ligand media which is synthesized in Example 1.

The anti-A IgM monoclonal antibody static binding capacity was then compared with the percentage removal of anti-A antibodies from an IVIG feed with the same media under the same conditions.

As summarized in Table 1 below, this experiment demonstrates that the batch-to-batch variation in static binding capacity of the various TriA ligand media for anti-A IgM monoclonal antibody correlates with batch-to-batch variation in the percentage anti-A IgG removal from an IVIG feed under static binding conditions. It was found that the TriA ligand media with higher capacity for monoclonal anti-A IgM, removed more anti-A IgG antibodies from an IVIG feed. It was also found that the TriA ligand media with lower static binding capacity for monoclonal anti-A IgM, removed less anti-A IgG antibodies from an IVIG feed.

This result was unexpected due to the differences in the type and source of the two molecules, i.e., IgM is monoclonal, has a larger pentameric structure, and is of murine origin while the IgG removed from the IVIG feed is polyclonal, has a smaller monomeric structure, and is of human origin. Based on this result, it may be concluded that the static binding capacity of TriA ligand media for anti-A IgM monoclonal antibody can be used as an indicia to evaluate the variation in batch-to-batch quality of an media which removes or is expected to remove a percentage of anti-A antibodies from a sample, e.g., during and after media manufacturing.

TABLE 1

The static biding capacities of three different TriA media for monoclonal anti-A IgM and the percentage of anti-A IgG removal from an IVIG feed.

| | monoclonal anti-A IgM static binding capacity (mg/mL) | percentage of anti-A IgG removed from an IVIG feed |
|---|---|---|
| TriA Media #1 | 1.6 | 65% |
| TriA Media #2 | 8.6 | 93% |
| TriA Media #3 | 12.9 | 101% |

Example 6. Binding Capacity of Blood Group B Antigen Trisaccharide Ligand Media for Purified Murine Monoclonal IgM-B Antibody as a Measure of Media Quality This is a representative example demonstrating that the binding capacity of a blood group B antigen trisaccharide (TriB) ligand media for a purified murine monoclonal IgM-B antibody can be used to evaluate the variations in batch-to-batch quality of the media, e.g., during and after manufacturing.

The concentration of TriB ligands was varied during the coupling reaction with the solid support, which in this case were polyvinyl ether based beads. The beads were therefore expected to have differing amounts of the TriB ligands, which simulates the type of variation that is expected during the media manufacturing process.

The concentration of the ligand used was in the order of: TriB Media #1<TriB Media #2<TriB Media #3. Therefore, it was expected that IgM capacity would be the least for the TriB Media #1, followed by TriB Media #2, and greatest for TriB Media #3.

In this experiment, the static binding capacity of the various TriB ligand media for the anti-B antibody was measured and the value is compared with the percentage of Anti-B IgG antibody removed from an IVIG feed Gammanorm 16.5% (165 mg/mL, 20×20 mL, product number: 00 357 340, Octapharma AG).

A set of 2.0 mL microcentrifuge tubes were filled with 0.35 mL of 10 mM PBS buffer or 0.50 mL of 10 mM PBS buffer for the controls. 0.15 mL of a 10% suspension of the polyvinyl ether based beads (15 μL media volume) in 10 mM PBS buffer was added to the microcentrifuge tubes, except for the controls. Subsequently, 1.0 mL of a 1 mg/mL anti-B IgM monoclonal antibody solution in 10 mM PBS buffer was added to all the tubes. The tubes were allowed to rotate for 4 hours at room temperature. Then the microcentrifuge tubes were subjected to centrifugation and then the supernatant was transferred into centrifugal filtration devices with a 0.22 micron membrane. The devices were subjected to centrifugation and the absorbance of the filtrate was measured at 280 nm. The solution absorbance of each sample was used to calculate the media's static binding capacity for anti-B IgM monoclonal antibody.

The anti-B IgM static binding capacity was calculated based on an extinction coefficient of 1.44 at 280 nm, estimated based on the protein's amino acid composition. The anti-B IgM monoclonal antibody static binding capacity was subsequently compared with the percentage removal of anti-B IgG antibodies from an IVIG feed under static binding conditions.

Blood group B antigen polyclonal IgG antibody (anti-B) level in a representative IVIG feed was determined by an established flow cytometry method (Christensson, M. et al, Transfusion, 1996, 36, 500-505). Type B red blood cells were incubated with the representative IVIG feed for a pre-determined time, followed by extensive washes. The cells were then stained with fluorescence-labeled anti-human IgG (Alexa Fluor® 488 AffiniPure F(ab')$_2$ Fragment Goat Anti-Human IgG (H+L), part number: 109-546-088, Jackson ImmunoResearch, West Grove, Pa., USA), and subjected to Flow Cytometry (Guava 5HT, EMD Millipore). Net mean fluorescence intensity (MFI) values were used to compare anti-B polyclonal IgG concentrations in the feed before and after contact with the blood group B trisaccharide antigen ligand media which is synthesized in Example 2.

As summarized in Table 2 below, this experiment demonstrates that the batch-to-batch variation in static binding capacity of the various TriB ligand media for anti-B IgM monoclonal antibody correlates with the batch-to-batch variation in percentage anti-B IgG removal from an IVIG feed under static binding conditions. It was found that the TriB ligand media with higher capacities for monoclonal anti-B IgM removed more anti-B IgG antibodies from an IVIG feed. It was also found that the TriB ligand media with lower static binding capacities for monoclonal anti-B IgM removed less anti-B IgG antibodies from an IVIG feed.

This data demonstrates the unexpected finding that the static binding capacity of TriB ligand media for a purified anti-B IgM monoclonal antibody can be used to assess the batch-to-batch variation in media quality, e.g., before and after manufacturing.

TABLE 2

Capacity of three different TriB media for monoclonal anti-B IgM and the percentage of anti-B IgG removed from an IVIG feed.

| | monoclonal anti-B IgM static binding capacity (mg/mL) | percentage of anti-B IgG removed from an IVIG feed |
|---|---|---|
| TriB Media #1 | 2.1 | 82% |
| TriB Media #2 | 7.4 | 93% |
| TriB Media #3 | 13.5 | 96% |

Example 7. Binding Capacity of Blood Group A Antigen Trisaccharide Ligand Media for a Purified Murine Monoclonal IgM-A Antibody as a Way to Monitor Media Quality Following Exposure to Caustic Cleaning Conditions This is a representative example demonstrating that the capacity of blood group A antigen trisaccharide (TriA) ligand medias for a purified murine monoclonal IgM-A antibody is a useful method to monitor the media's quality after exposure to harsh caustic cleaning conditions.

A solution of 1.0 M sodium hydroxide was flowed at 0.5 mL/min over packed columns of TriA ligand media (5.0 mL, 1.0 cm diameter and 6.4 cm in length) at 0 hours, 50 hours, or 150 hours. The media was then neutralized with 10 mM PBS until the pH of the solution exiting the column was approximately pH 7. The static binding capacity of the three TriA ligand media for the anti-A IgM monoclonal antibody was then measured and compared with the percentage removal of anti-A IgG from an IVIG feed using the same media.

A set of 2.0 mL microcentrifuge tubes were filled with 0.35 mL of 10 mM PBS buffer or 0.50 mL of 10 mM PBS buffer for the controls. 0.15 mL of a 10% suspension of the media (15 μL media volume) in 10 mM PBS buffer was added to the microcentrifuge tubes, except for the controls. Subsequently, 1.0 mL of a 1.0 mg/mL anti-A IgM monoclonal antibody solution in 10 mM PBS buffer was added to each of the tubes. The tubes were allowed to rotate for 4 hours at room temperature. The microcentrifuge tubes were subjected to centrifugation and the resultant supernatant was transferred into centrifugal filtration devices with a 0.22 micron membrane. The devices were subjected to centrifugation and the absorbance of the filtrate was measured at 280 nm. The solution absorbance of each sample was then used to calculate the media's static binding capacity for anti-A IgM monoclonal antibody.

The anti-A IgM static binding capacity was calculated based on an extinction coefficient of 1.50 at 280 nm, estimated based on the protein's amino acid composition. The anti-A IgM monoclonal antibody static binding capacity was then compared with the percentage of anti-A IgG antibodies removed from an IVIG feed under static binding conditions using the same media.

Blood group A antigen polyclonal IgG antibody concentration in a representative IVIG feed was determined using an established flow cytometry method (Christensson, M. et al, Transfusion, 1996, 36, 500-505). Type A red blood cells were incubated with IgG concentrates for a pre-determined time, followed by extensive washes. The cells were then stained with fluorescence-labeled anti-human IgGs (Alexa Fluor® 488 AffiniPure F(ab')$_2$ Fragment Goat Anti-Human IgG (H+L), part number: 109-546-088, Jackson ImmunoResearch, West Grove, Pa., USA), and subjected to Flow Cytometry (Guava 5HT, EMD Millipore). Net mean fluorescence intensity (MFI) values were used to compare anti-A polyclonal IgG concentrations in samples before and after contact with the blood group A trisaccharide antigen ligand media.

As summarized in Table 3 below, this experiment demonstrates that the relative differences in the static binding capacity of the various TriA ligand media for monoclonal anti-A IgM correlates with the relative differences in the percentage of anti-A IgG removal from an IVIG feed. It was observed that the longer the TriA ligand media was exposed to the caustic cleaning conditions, the lower its static binding capacity was found to be for monoclonal anti-A IgM and less anti-A IgG antibody was removed from an IVIG feed.

Accordingly, the static binding capacity of TriA ligand media for monoclonal anti-A IgM can be used to monitor the quality of this type of media following exposure to caustic conditions.

TABLE 3

Capacity of a TriA ligand media for monoclonal anti-A IgM and the percentage of anti-A IgG removal from an IVIG feed following exposure to 1.0M sodium hydroxide for various lengths of time.

| length of time exposed to 1.0M sodium hydroxide (hours) | monoclonal anti-A IgM static binding capacity (mg/mL) | percentage of anti-A IgG removed from an IVIG feed |
| --- | --- | --- |
| 0 | 19.7 | 77% |
| 50 | 18.1 | 65% |
| 150 | 10.2 | 40% |

Example 8. Binding Capacity of Blood Group B Antigen Trisaccharide Ligand Media for a Purified Monoclonal Murine Monoclonal IgM-B as a Way to Monitor Media Quality After Exposure to Caustic Cleaning Conditions This is a representative example demonstrating that the capacity of blood group B antigen trisaccharide (TriB) ligand media for a purified murine monoclonal IgM-B antibody is a useful method to monitor the media's quality after exposure to harsh caustic cleaning conditions.

A solution of 1.0 M sodium hydroxide was flowed at 0.5 mL/min over packed columns of TriB ligand media (5.0 mL, 1.0 cm diameter and 6.4 cm length) at 0 hours, 50 hours, or 150 hours. The media was then neutralized by flowing 10 mM PBS through the column until the pH of solution exiting the column was approximately pH 7. The static binding capacity of the three TriB ligand medias for the monoclonal anti-B IgM was then measured and compared with the percentage removal of anti-B IgG from an IVIG feed using the same medias.

A set of 2.0 mL microcentrifuge tubes were filled with 0.35 mL of 50 mM PBS buffer or 0.50 mL of 10 mM PBS buffer for the controls. 0.15 mL of a 10% suspension of the media (15 μL media volume) in 10 mM PBS buffer was added to the microcentrifuge tubes, except for the controls. Subsequently, 1.0 mL of a 1.0 mg/mL anti-B IgM monoclonal antibody solution in 10 mM PBS buffer was added to each of the tubes. The tubes were allowed to rotate for 4 hours at room temperature. Then the microcentrifuge tubes were subjected to centrifugation and the resulting supernatant was transferred into centrifugal filtration devices with a 0.22 micron membrane. The devices were subjected to centrifugation and then the absorbance of the filtrate was measured at 280 nm. The solution absorbance of each sample was then used to calculate the media's static binding capacity for anti-B IgM monoclonal antibody. The anti-B IgM static binding capacity was calculated based on an extinction coefficient of 1.44 at 280 nm, estimated based on the protein's amino acid composition. The anti-B IgM monoclonal antibody static binding capacity was then compared with the percentage removal of anti-B IgG antibody from an IVIG feed.

Blood group B antigen polyclonal IgG antibody concentration in a representative IVIG feed was determined using an established flow cytometry method (Christensson, M. et al, Transfusion, 1996, 36, 500-505). Type B red blood cells were incubated with IgG concentrates for a pre-determined time, followed by extensive washes. The cells were then stained with fluorescence-labeled anti-human IgG (Alexa Fluor® 488 AffiniPure F(ab')$_2$ Fragment Goat Anti-Human IgG (H+L), part number: 109-546-088, Jackson ImmunoResearch, West Grove, Pa., USA), and subjected to Flow Cytometry (Guava 5HT, EMD Millipore). Net mean fluorescence intensity (MFI) values were used to compare anti-A polyclonal IgG concentrations in samples before and after contact with the blood group A trisaccharide antigen ligand media.

As summarized in Table 4 below, this experiment demonstrates that the relative differences in the static binding capacity of the various TriB ligand media for purified monoclonal anti-B IgM antibody correlates with the relative differences in the percentage of anti-B IgG removal from an IVIG feed. It was found that the length of time that the TriB ligand media was exposed to the caustic cleaning conditions did not greatly influence its static binding capacity for monoclonal anti-B IgM or the amount of anti-B IgG antibodies that were removed from an IVIG feed under static binding conditions. The data indicates the unexpected result that the static binding capacity of TriB ligand media for monoclonal anti-B IgM can be used to monitor the quality of this type of media.

TABLE 4

Capacity of TriB ligand media for monoclonal anti-B IgM and the percentage of anti-B IgG removed from an IVIG feed after exposure to 1.0M sodium hydroxide for various lengths of time.

| length of time exposed to 1.0M sodium hydroxide (hours) | Monoclonal anti-B IgM static binding capacity (mg/mL) | percentage of anti-B IgG removed from an IVIG feed |
| --- | --- | --- |
| 0 | 19.0 | 79% |
| 50 | 18.9 | 76% |
| 150 | 19.3 | 76% |

Example 9. Distinguishing Between Blood Group A and Blood Group B Antigen Trisaccharide Ligand Media by Measuring their Static Binding Capacities for Purified Murine Monoclonal Antibodies IgM-A and IgM-B, Respectively This is a representative example demonstrating that the relative static binding capacities of blood group A antigen trisaccharide (TriA) ligand media and blood group B antigen trisaccharide (TriB) ligand media for murine monoclonal antibodies IgM-A and IgM-B, respectively, can be used to differentiate between the two types of media.

The ability to readily differentiate between the two types of media is useful since the two media are typically used together for the removal of anti-A and anti-B antibodies from blood and plasma products and can be easily mixed up. Differentiation was demonstrated by measuring the static binding capacity of a TriA ligand media and a TriB ligand media for both monoclonal anti-A IgM and monoclonal anti-B IgM.

A set of 2.0 mL microcentrifuge tubes were filled with 0.35 mL of 50 mM PBS buffer or 0.50 mL of 50 mM PBS buffer for the controls. 0.15 mL of a 10% suspension of the media (15 μL media volume) in 50 mM PBS buffer was added to the microcentrifuge tubes, except for the controls. Subsequently, 1.0 mL of a 1.0 mg/mL anti-A IgM monoclonal antibody solution in 50 mM PBS buffer or 1.0 mL of a 1.0 mg/mL anti-B IgM monoclonal antibody solution in 50 mM PBS buffer was added to each of the tubes. The tubes were allowed to rotate for 4 hours at room temperature. Then the microcentrifuge tubes were subjected to centrifugation and the resulting supernatant was transferred into centrifugal filtration devices with a 0.22 micron membrane. The devices were subjected to centrifugation and then the absorbance of the filtrate was measured at 280 nm. The solution absorbance of each sample at 280 nm was used to calculate the media's static binding capacity for anti-A IgM monoclonal antibody and anti-B IgM monoclonal antibody. The anti-A IgM static binding capacities were calculated based on an extinction coefficient of 1.50 at 280 nm, estimated based on the protein's amino acid composition. The anti-B IgM static binding capacity was calculated based on an extinction coefficient of 1.44 at 280 nm, estimated based on the protein's amino acid composition.

As summarized in Table 5 below, this experiment demonstrates that the identity of media capable of binding anti-A antibodies or capable of binding anti-B antibodies can be differentiated by measurement of their binding capacity for both anti-A IgM monoclonal antibody and anti-B IgM monoclonal antibody.

It was observed that the TriA ligand media had significant binding capacity for the anti-A IgM monoclonal antibody while it had very low binding capacity for anti-B IgM monoclonal antibody. In contrast, it was observed that the TriB ligand media had significant binding capacity for anti-B IgM monoclonal antibody while it had very low binding capacity for the anti-A IgM monoclonal. In this way, A-antigen ligand media and B-antigen ligand media can be easily distinguished, especially in instances, when the identity of such media samples is unknown.

TABLE 5

Capacity of TriA ligand media and TriB ligand media for both monoclonal anti-A IgM and anti-B monoclonal IgM.

| | monoclonal anti-A IgM static binding capacity (mg/mL) | monoclonal anti-B IgM static binding capacity (mg/mL) |
|---|---|---|
| TriA media | 21.1 | 0.3 |
| TriB media | 0.2 | 21.1 |

Example 10. Generating and Assessing the Relative Quality of a Mixture of Media Based on Binding Capacities for Purified IgM-A or IgM-B Monoclonal Antibodies As observed herein, the relative binding capacity of a blood group A antigen media or a blood group B antigen media to purified monoclonal IgM-A or IgM-B antibodies is a good indicia to assess or predict how such media may actually perform for the removal of blood group A antigen antibodies or blood group B antigen antibodies from a sample (e.g., blood, blood product, plasma or IVIG).

The relative binding capacity of a blood group A antigen media for purified monoclonal IgM-A and the relative binding capacity of a blood group B antigen media to or IgM-B antibodies could be used to generate a mixture of both media in the right proportion, which can then be used to remove both blood group A antigen antibodies and blood group B antigen antibodies from a sample in one chromatography step.

This is particularly useful as generally, the amounts of blood group A antigen antibodies and blood group B antigen antibodies tend to vary from sample to sample. Therefore, a mixture of media which may work well for removal of such antibodies from one sample may not work as well in case of another sample.

The methods described herein can be used to design a mixture of media which would work well for a sample, by simply knowing the amounts of anti-A and anti-B antibodies in that sample.

For example, since the binding capacity of a media for purified monoclonal IgM antibody correlates with the percentage removal of anti-A or anti-B antibodies from a sample, once the level or amount of anti-A and anti-B antibodies in a sample is known, a mixture of media or media can be designed, such that to have a ratio of the blood group A antigen media and a blood group B antigen media, which would be suitable to remove a desired amount of anti-A and/or anti-B antibodies from the sample, based on the binding capacity for the respective IgM molecules.

The methods described herein can also be used to determine the relative quality of a mixture of media composed of media having blood group A antigen ligands and media having blood group B antigen ligands.

The specification is most thoroughly understood in light of the teachings of the references cited within the specification which are hereby incorporated by reference. The embodiments within the specification provide an illustration of embodiments and should not be construed as limiting in scope. The skilled artisan (practitioner) readily recognizes that many other embodiments are encompassed by this disclosure. All publications and reference materials are incorporated by reference in their entirety. To the extent that the material incorporated by reference contradicts or is inconsistent with the present specification, the present specification will supercede any such material. The citation of any references herein is not an admission that such references are prior art.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the embodiments disclosed herein. Unless otherwise indicated, the term "at least" preceding a series of elements is to be understood to refer to every element in the series. Those skilled in the art will recognize, or be able to ascertain using no more than routine experimentation, many equivalents to the specific embodiments described herein. Such equivalents are intended to be encompassed by the following claims.

Many modifications and variations of the embodiments disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the disclosure being indicated by the following claims.

What is claimed is:

1. Method of comparing quality of two or more affinity chromatography media samples containing blood group A antigen ligands attached to a solid support, the method comprising the steps of:
    (a) for each of the media samples, providing a solution of purified monoclonal IgM-A antibody of known concentration C1 and volume VM and an affinity chromatography media sample of volume VR;
    (b) incubating each chromatography media sample with the solution of (a);
    (c) obtaining a supernatant and measuring the concentration C2 of the IgM-A antibody in the supernatant, for each chromatography media sample;
    (d) determining the static binding capacity of each chromatography media sample for the IgM-A antibody, wherein the static binding capacity is measured using the equation $$\frac{[C1-C2] \times VM}{VR}$$

wherein the static binding capacities of the media samples correlates with their ability to remove anti-A antibodies from a sample, thereby providing a comparison of the quality of two or more different affinity chromatography media samples; and
    (e) purifying blood or a blood derived product with a media sample determined by step (d) to provide media capable of selectively removing antibodies.

2. Method of comparing quality of two or more affinity chromatography media samples containing blood group B antigen ligands attached to a solid support, the method comprising the steps of:
    (a) for each of the media samples, providing a solution of purified monoclonal IgM-B antibody of known concentration C1 and volume VM and an affinity chromatography media sample of volume VR;
    (b) incubating each chromatography media sample with the solution of (a);
    (c) obtaining a supernatent and measuring the concentration C2 of the IgM-B antibody in the supernatant, for each chromatography media sample;
    (d) determining the static binding capacity of each chromatography media sample for the IgM-B antibody, wherein the static binding capacity is measured using the equation:

$$\frac{[C1-C2] \times VM}{VR}$$

wherein the static binding capacities of the media samples correlates with their ability to remove anti-B antibodies from a sample, thereby providing a comparison of the quality of two or more affinity chromatography media samples; and
    (e) purifying blood or a blood derived product with a media sample determined by step (d) to provide media capable of selectively removing antibodies.

3. The method of claim 1, wherein the solid support is a porous or non-porous polymeric solid support comprising a polymer selected from the group consisting of polyvinylether, polyvinylalcohol, polymethacrylate, polyacrylate, polystyrene, polyacrylamide, polymethacrylamide and polycarbonate.

4. The method of claim 2, wherein the solid support is a porous or non-porous polymeric solid support comprising a polymer selected from the group consisting of polyvinylether, polyvinylalcohol, polymethacrylate, polyacrylate, polystyrene, polyacrylamide, polymethacrylamide and polycarbonate.

5. The method of claim 1, wherein the solid support is a polyvinylether based porous solid support.

6. The method of claim 2, wherein the solid support is a polyvinylether based porous solid support.

7. The method of claim 5, wherein the polyvinylether based porous solid support is in bead form.

8. The method of claim 6, wherein the polyvinylether based porous solid support is in bead form.

9. The method of claim 1, wherein the binding capacity of the blood group A antigen ligand media for monoclonal IgM-A antibody correlates with its ability to remove anti-A antibodies from a sample.

10. The method of claim 2, wherein the binding capacity of the blood group B antigen ligand media for monoclonal IgM-B antibody correlates with its ability to remove anti-B antibodies from a sample.

11. The method of claim 1, wherein the two or more affinity chromatography media samples constitute different batches of the same media.

12. The method of claim 2, wherein the two or more affinity chromatography media samples constitute different batches of the same media.

13. The method of claim 1, wherein the different affinity chromatography media samples constitute the same media at different stages of use.

14. The method of claim 2, wherein the different affinity chromatography media samples constitute the same media at different stages of use.

15. The method of claim 9, wherein the sample is selected from the group consisting of blood, blood products, plasma, plasma derivatives and IVIG feed.

16. The method of claim 10, wherein the sample is selected from the group consisting of blood, blood products, plasma, plasma derivatives and IVIG feed.

17. The method of claim 1, wherein the measurement of concentration comprises determining absorbance at 280 nm.

18. The method of claim 2, wherein the measurement of concentration comprises determining absorbance at 280 nm.

19. A method of assessing quality of a media following exposure to acid or alkaline conditions, wherein the method comprises the steps of:
    (a) providing a chromatography media having wither blood group A antigen ligands or blood group B antigen ligands attached to a solid support;
    (b) measuring, via absorbance at a particular wavelength, the binding capacity of the media for a purified IgM-A antibody in case of blood group A antigen antibody or for a purified IgM-B antibody in case of blood group B antigen antibody;
    (c) exposing the media to acid or alkaline conditions for at least 5 hours; and (d) measuring the binding capacity of the media for a purified IgM-A antibody in case of blood group A antigen antibody or for a purified IgM-B antibody in case of blood group B antigen antibody;

wherein a reduction in the binding capacity of media in (d) relative to (b) indicates that the quality of media has decreased following exposure to acid of alkaline conditions.

20. The method of claim 19, wherein a decrease in quality of media comprises a reduction in the ability of media to remove anti-A of anti-B antibodies.

21. Method of determining whether a media comprises blood group A antigen ligands or blood group B antigen ligands, wherein the method comprises the steps of:

(a) providing a media, wherein it is unknown whether the media comprises blood group A antigen ligands or blood group B antigen ligands;

(b) measuring, via absorbance at a particular wavelength, the binding capacity of the unknown media for purified monoclonal IgM-A antibody and separately for purified monoclonal IgM-B antibody; and (c) comparing the capacity of the unknown media for purified monoclonal IgM-A antibody and purified monoclonal IgM-B antibody;

wherein the unknown media is determined to comprise blood group A antigen ligands, if it has a higher binding capacity for monoclonal IgM-A antibody relative to binding capacity for monoclonal IgM-B antibody, and the unknown media is determined to comprise blood group B antigen ligands if it has a higher binding capacity for monoclonal IgM-B antibody relative to binding capacity for monoclonal IgM-A antibody.

* * * * *